United States Patent [19]
Ely et al.

[11] Patent Number: 5,514,410
[45] Date of Patent: May 7, 1996

[54] PYROCARBON AND PROCESS FOR DEPOSITING PYROCARBON COATINGS

[75] Inventors: John L. Ely, Austin; Axel D. Haubold, Liberty Hill; Michael R. Emken, Austin; James A. Accuntius, Georgetown, all of Tex.

[73] Assignee: Carbon Implants, Inc., Austin, Tex.

[21] Appl. No.: 303,064

[22] Filed: Sep. 8, 1994

[51] Int. Cl.⁶ .............. B05D 7/24; B05D 3/02; B05D 3/04
[52] U.S. Cl. .............. 427/2.24; 427/213; 427/228; 427/249
[58] Field of Search ............... 427/2.24, 249, 427/213, 228, 378, 255.1, 255.5

[56] References Cited

U.S. PATENT DOCUMENTS

| | | | |
|---|---|---|---|
| 3,399,969 | 9/1968 | Bokros et al. | 23/209.1 |
| 3,547,676 | 12/1970 | Bokros et al. | 427/213 |
| 3,676,179 | 7/1972 | Bokros | 117/46 |
| 3,677,795 | 7/1972 | Bokros et al. | 427/2.24 |
| 3,685,059 | 8/1972 | Bokros et al. | 3/1 |
| 3,707,006 | 12/1972 | Bokros et al. | 3/1 |
| 3,969,130 | 7/1976 | Bokros | 427/2.24 |
| 3,977,896 | 8/1976 | Bokros et al. | 427/213 |
| 4,101,984 | 7/1978 | MacGregor | 427/2.24 |
| 4,126,924 | 11/1978 | Akins et al. | 427/2.26 |
| 4,194,027 | 3/1980 | Adams et al. | 427/249 |
| 4,594,270 | 6/1986 | Brooks | 427/213 |
| 5,258,022 | 11/1993 | Davidson | 427/2.24 |
| 5,262,104 | 11/1993 | Schwartz | 427/249 |
| 5,284,676 | 2/1994 | Accuntius | 427/213 |
| 5,328,713 | 7/1994 | Emken et al. | 427/8 |
| 5,328,720 | 7/1994 | Emken | 427/249 |

FOREIGN PATENT DOCUMENTS 0055406  3/1985  European Pat. Off. .

OTHER PUBLICATIONS

Bokros, et al.; "Carbon In Prosthetic Devices" *Petroleum Derived Carbons*, ACS Symposium Series, No. 21, pp. 237–265, (1975) no month available.

Shim, et al.; "The Wear Resistance of Pure and Silicon-Alloyed Isotropic Carbons" *Biomat., Med. Dev., Art. Org.*, 2(2), pp. 103–118, (1974) no month available.

Gilpin, et al.; "Fatigue Crack Growth and Fracture of Pyrolytic Carbon Composites" *Bioceramics*, vol. 6, pp. 217–223, (1993) no month available.

Emken, et al.; "Precise Control of Pyrolytic Carbon Coating" submitted to 21st Biennial Conference on Carbon, Buffalo, N.Y., Jun. 13–18, 1993.

Akins, et al.; "Final Technical Report for the Period Jan. 1, 1974 to Dec. 31, 1974," Carbon Research, Advanced Research Projects Agency (ARPA), Feb. 28, 1975.

*Primary Examiner*—Diana Dudash
*Attorney, Agent, or Firm*—Fitch, Even, Tabin & Flannery

[57] ABSTRACT

Pure unalloyed pyrocarbons having wear resistance suitable for use in pyrocarbon-coated heart valve components and having mechanical properties, such as flexural strength and toughness, superior to commercial silicon-alloyed pyrocarbons are deposited in fluidized bed coaters. Coating conditions are carefully controlled so as to maintain a precise bed size within a defined coating enclosure which will assure a substantially constant surface deposition temperature that in turn assures deposition of homogenous unalloyed pyrocarbons having these improved mechanical properties.

19 Claims, 1 Drawing Sheet

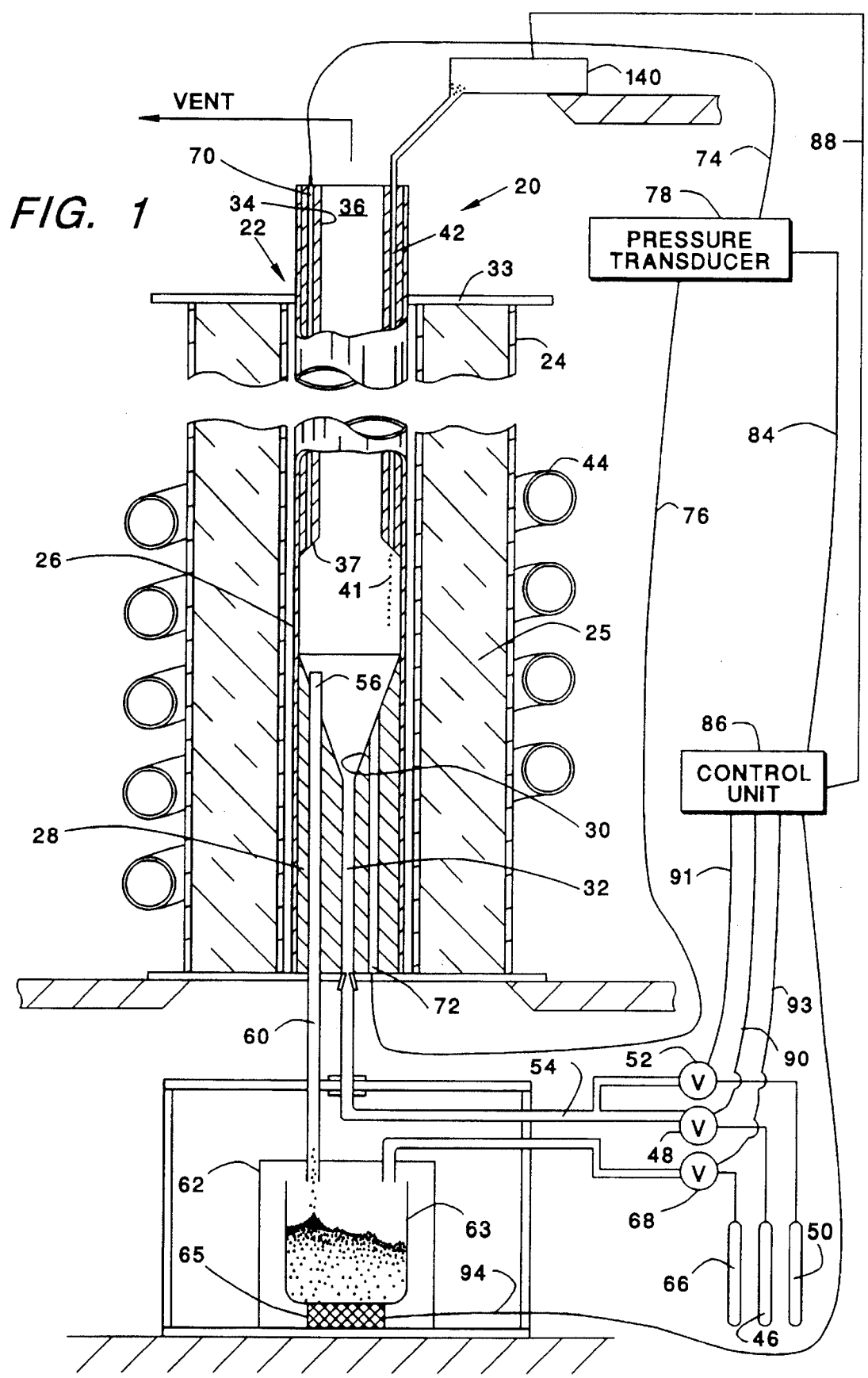

PYROCARBON AND PROCESS FOR DEPOSITING PYROCARBON COATINGS

BACKGROUND OF THE INVENTION

This invention relates to pyrocarbon and to processes for depositing pyrocarbon coatings on substrates in a fluidized bed. More particularly, the invention relates to processes for depositing pure, unalloyed pyrocarbon having improved physical properties on substrates being levitated in a coating region along with a bed of small particles and also to pyrocarbon having improved mechanical properties heretofore obtained only in silicon-alloyed pyrocarbon structures.

BACKGROUND OF THE INVENTION

Pyrolytic carbon, i.e. pyrocarbon, coatings were developed some 30 years ago as coatings for minute spheroids of nuclear fuel to be used in high temperature gas-cooled fission reactors, and substantial effort was expended in attempting to improve the properties of these pyrocarbons for such purposes. Of particular interest was the mechanical strength and the stability of the pyrocarbon under high level neutron radiation. Examples of U.S. patents illustrative of such pyrocarbon coatings and processes for depositing these coatings include U.S. Pat. No. 3,325,363 (Jun. 13, 1967) and U.S. Pat. No. 3,547,676 (Dec. 15, 1970).

Subsequently, it was unexpectedly discovered that pyrocarbon of a specific character, i.e., having relatively high density of at least about 1.5 gm/cm$^3$, having an apparent crystallite size of about 200 Å or less and having high isotropy, exhibited remarkably good properties for use in devices that would have direct or indirect contact with the circulatory system of humans because such pyrocarbon was outstandingly inert and did not give rise to thrombosis. As a result, such pyrocarbon coatings have become the materials of choice for prosthetic heart valves and other components of apparatus for interconnection with the circulatory system of humans. U.S. Pat. No. 3,685,059 is indicative of such pyrocarbons.

Although such pyrocarbons were expected to have reasonably good hardness and structural strength, it has uniformly been felt that, in order to assure adequate structural strength required for many biomedical purposes, it was necessary to add a carbide-forming alloying element, such as the metalloid silicon which would form silicon carbide. It has thus become common to employ up to about 20 weight percent of silicon which was found to provide the alloyed pyrocarbon with hardness, wear-resistance and overall structural strength sufficient to meet established criteria; such use of silicon is pointed out in the '059 patent at Column 5, which also describes other carbide-forming elements which could alternatively be used as additives. Most frequently, such an alloying element was used in an amount from about 1 and 6 atom percent, based upon total atoms of carbon plus the element. Typically, pyrocarbon coatings for heart valve components which have been used in commercial heart valves in the United States over the past decade have included from about 5 to about 12 weight percent of silicon. The addition of silicon was generally carried out by adding methyltrichlorosilane to the upwardly flowing stream of a mixture of hydrocarbon and inert gas that was being used to deposit the coating. It is believed that all FDA-approved pyrocarbon coatings for heart valve components include at least about 5 weight percent silicon carbide for the purpose of increasing hardness and wear resistance.

Unfortunately, silicon carbide is not as nonthrombogenic as pyrocarbon. Although it has been acceptable for the pyrocarbon coatings to include a minor amount of silicon carbide as an alloying agent, because silicon carbide does exhibit some thrombogenicity, the biocompatibility of pyrocarbon coatings with the bloodstream could be improved if heart valve components could instead be coated with pure, unalloyed pyrocarbon. Significant processing improvements would also occur in the pyrocarbon deposition process if it were not necessary to handle a potentially corrosive substance, such as methyltrichlorosilane or the like; such an elimination would reduce both capital costs and operating costs. Not only would the cost of this additional raw material be eliminated, but the cost of the tubing network and control necessary to inject or supply precise amounts of a chlorosilane into the levitating gas stream would be eliminated. It would also reduce many of the safety precautions necessary in such a coating operation as well as in the cleanup steps upon the completion of a coating run.

Studies were carried out in about 1974 relating to the character of pyrocarbon deposited at various temperatures in expanding beds from gaseous atmospheres containing different volume percents of a variety of hydrocarbons, and the results were published in a U.S. Government (Advanced Research Projects Agency) report No. GA-A13350—Carbon Research—Final Technical Report for the Period Jan. 1, 1974 to Dec. 31, 1974. Because such a growing bed would fairly soon collapse, coatings only about 1 mil in thickness were generally obtained. Unalloyed pyrocarbons deposited in such study using a low volume % of propane at a sight port temperature of 1350° C. were reported to have a density of about 1.46 g/cm$^3$, a crystallite size of about 20 Å and a DPH hardness of about 153. The hardness number is a standard Diamond Pyramid Hardness measured with a 50 gram load. By increasing the propane to 60 volume % at this temperature, a carbon density of about 1.97 was obtained for these thin pyrocarbon samples, with a crystallite size of about 36 Å and a hardness of about 219 DPH. In contrast by adding 8 weight % silicon to pyrocarbon of about 1.97 density the DPH hardness rises dramatically to about 295. On the other hand when the sight port temperature is raised to about 1475° C. (bed temperature about 1400° C.), the density decreases to about 1.46, the hardness to about 92 DPH and the crystallite size to about 26 Å. Young's modulus, fracture strength and hardness were all shown to generally rise with increasing density, and it was also shown that denser (and harder) carbons provided higher wear resistance. One conclusion of the study was that hardness and thus wear resistance of carbons increased with increasing density which would favor the lower temperature isotropic carbons; however, it was felt that a significant reduction in wear rate was more easily obtainable by alloying the pyrolytic carbon with silicon, which path has generally been followed.

Therefore, improved processes which would eliminate, or at least vastly lower, the amount of alloying silicon carbide needed to provide pyrocarbon with desired strength, resistance to cracking and hardness have long been desired.

SUMMARY OF THE INVENTION

It has now been found that, by depositing pyrocarbon under very carefully controlled conditions in a fluidized bed, pure, unalloyed pyrocarbon coatings having high fracture toughness, high strength, and high strain-to-failure, along with adequate hardness, can be provided. Because of the absence of any silicon carbide, such pure, unalloyed pyrocarbons have improved biocompatibility and outstanding nonthrombogenicity.

It was surprisingly found that such pure, unalloyed pyrocarbons of the foregoing characteristics can be consistently deposited in a fluidized bed if conditions can be carefully controlled within a fairly narrow temperature range above about 1325° C. and below or at about 1450° C. by carrying out the pyrolytic decomposition of a hydrocarbon gas that is being supplied, usually as a part of a levitating gas-coating mixture containing at least about 40 volume percent of inert levitating gas. Using propane, for example the preferred range is from about 1375° C. to about 1425° C. By maintaining a truly constant bed surface area, it has been found that the actual bed temperature at the surfaces where deposition is occurring can be precisely controlled and will result in isotropic, pure pyrocarbon of desired hardness and structural strength being consistently deposited in a fluidized bed coating zone. Thus, pyrocarbon coatings of adequate thickness and structural characteristics to permit their use in prosthetic devices, particularly heart valve prostheses, can be formed without the inclusion of a silicon alloying agent.

BRIEF DESCRIPTION OF THE DRAWING

FIG. 1 is a schematic view, partly in section, of a fluidized bed apparatus for depositing pyrocarbon onto objects being levitated in association with a bed of particles, which is exemplary of an apparatus that can be used to carry out processes for depositing pyrocarbon coatings embodying various features of the invention.

DETAILED DESCRIPTION OF PREFERRED EMBODIMENTS

A fluidized bed coating apparatus 20 is illustrated in FIG. 1 which includes a furnace 22 having an outer cylindrical shell 24 within which a coating enclosure is located. The coating enclosure is generally separated from the cylindrical outer shell of the furnace by a layer of insulation 25 and is defined generally by a thin sleeve or tube 26 in combination with a lower insert 28. The lower insert 28 mates with the bottom end of the thin tube 26 and provides the coating enclosure with a conical bottom surface 30; it includes a central passageway 32 that extends vertically upward therethrough and is preferably coaxial with the thin tube 26 which is of circular cross-section. Although there should be no size limitations on such coaters, of general interest are coaters having tubes 26 not greater than about a foot in diameter and particularly those having an interior diameter of about 6 inches or less. The levitating atmosphere flows upward through this passageway 32 to enter the coating enclosure.

The upper end of the furnace tube 24 includes a plate 33 which centers the coating tube 26 therewithin, and an exit passageway 36 from the coating enclosure is defined by an upper insert 34 which extends downward into the furnace and narrows the outlet opening somewhat, which insert has a frustoconical lower surface 37. The remainder of the mixture of hot levitating and coating gases leaving the fluidized bed coater pass through this upper exit passageway 36 and flow to an appropriate vent. A particle feeding device 40 is mounted generally above the fluidized bed coater 20 and is designed to feed minute particles 41 into the coating enclosure at a desired constant or variable rate. The particles from the feeder 40 enter the coater through an entrance conduit 42 which extends downward through the wall of the upper insert 34, terminating at the frustoconical surface 37. A suitable induction or alternating current heating device 44 is provided, as well known in this art. It is disposed in surrounding relationship to the furnace tube 24 in order to heat the active deposition region of the coating enclosure, together with the small particles that make up the bed and the objects being levitated in the bed, to bring them to the desired deposition temperature for pyrolytic coating.

The coating operation is carried out by establishing a levitated bed of minute particles, submillimeter in size, which is maintained in the lower region of the coating enclosure; this region is referred to as the active deposition region, or as the coating zone. As illustrated, the active deposition region generally occupies the conical region defined by the upper end surface 30 of the lower insert; however, depending upon the size of the bed employed, it may extend upward a few inches into the cylindrical section thereabove. Once the bed is established and brought up to coating temperature by applying an appropriate amount of electrical power to the heating unit 44, one or more objects to be coated, such as annular valve bodies or occluders for prosthetic heart valves, are appropriately loaded into the bed through the upper exit passageway 36 shortly before coating is ready to begin. Once in the bed, these objects are levitated and supported among the fluidized particles by the upwardly flowing gaseous stream, where they are likewise heated to raise their temperature to the desired coating temperature. The temperature within the coating enclosure is appropriately set and monitored as is well known in this art, as by using optical temperature-measuring devices, such as a sight-port pyrometer that functions with a viewing port in the furnace wall (not shown). It has been recognized that the temperature read by such a sight-port pyrometer will be somewhat above the actual bed temperature, which can be accurately read electrically (e.g. by thermocouples); however, it has now been found that the bed temperature can change substantially when changes in the bed surface area occur, which can dramatically affect the properties of the pyrocarbon being deposited.

The upwardly flowing gas stream, during the time of coating, is made up of a mixture of an inert fluidizing gas plus a gaseous hydrocarbon, as described hereinafter. Illustrated is a source of hydrocarbon 46 which is provided with a flow-regulating valve arrangement 48 alongside a source 50 of inert gas, for example argon, helium or nitrogen, which is likewise equipped with a suitable flow-regulating valve arrangement 52. These two gas sources flow into a common line 54 which leads to the vertical passageway 32 in the lower insert 28.

The total flow of levitating-coating gas upward through the coating enclosure is regulated so that the fluidized bed occupies an active deposition region which generally fills the conical region at the top of the insert 28 and may extend a few inches upward into the cylindrical tube 26 for larger beds. The upward flow of the gaseous stream through the central passageway causes a generally toroidal flow pattern to be established within the lower region of the fluidized bed, which is defined generally by the conical surface 30 of the insert 28, with the minute particles traveling upward in the central region and then downward generally along the outer perimeter of this toroidal flow pattern.

The particles may be chosen so as to have a density greater than the density of the pyrocarbon being deposited in the bed. The particles are about 1,000 microns (μm) or less in size, and preferably, the original bed is constituted by particles not greater than about 850 microns. The particles added during the coating run preferably have an average size not greater than about 400 microns. Generally particles between about 300 and about 425 microns are added during the coating run, and the average size of the particles withdrawn over the coating run is greater than about 500 μm.

To remove particles from the bed, an exit conduit 56 is provided having a circular access opening of a suitable diameter in its upper end. The conduit 56 can extend through the entire lower insert 28, or it can be shorter in length and be received in a coaxial counterbore provided at the upper end of a drilled passageway where it will protrude from the conical surface 30 of the insert. The exit conduit 56 may open straight up or be capped at its upper end and have an exit hole in its sidewall as earlier described in this art. The conduit 56 may be proportioned so that its upper end terminates within the vertical region defined by the conical surface 30, and preferably, the conduit 56 protrudes from the conical surface 30 a maximum vertical distance of less than about 1 inch for a coater having an interior diameter of about 4 inches or less. The exit conduit 56, which extends into the coating region, is formed of a suitable refractory material, such as graphite or mullite.

Particles being removed from the fluidized bed, which enter the conduit 56 through such an access opening, fall downward by gravity to a discharge conduit 60 leading to a collection chamber 62 where they are received in a graduated cylinder 63 or the like so that the total amount and/or volume of particles having been removed can be determined at any time either visually or through the use of a load cell 65. The collection chamber 62 is pressurized with inert gas from a suitable source 66 which is precisely controlled through the use of a flow-regulating valve arrangement 68 that is suitably set by a control arrangement discussed in detail hereinafter. The flow of inert gas out of the pressurized collection chamber upward through discharge tube 60 and the exit conduit 56 serves both as a purge flow to prevent substantial quantities of dust from falling into the collection chamber and also to precisely regulate the rate of removal of particles from the fluidized bed. By increasing the gas pressure within the collection chamber 62, the rate of upward flow of inert gas will increase, with a resultant decrease in the rate, or a total cessation, of withdrawal of particles from the bed. Decrease of gas pressure, continuously or periodically, increases rate of withdrawal of particles over time. Feeding particles at a constant rate and withdrawing particles at a relatively constant rate should permit the amount of particles in the bed to be maintained at a precise predetermined level throughout a coating run.

It has been found that maintaining the surface area of the fluidized particle bed within a coating enclosure in the region where the coating deposition is occurring is a most important parameter in precisely controlling the rate of deposition and the character of the pyrocarbon being deposited. Measurement of the pressure difference ($\Delta P$) across the fluidized bed so as to detect changes that occur is one effective way of sensing even small changes in the overall surface area of the bed. By monitoring the pressure difference across the bed, i.e. between a point at a lower region in the bed or just below the bed and a point above the bed, to detect changes which occur and then responding to such detected changes from the desired target value to compensate for such, precise control of the pyrocarbon being deposited throughout a coating run is achieved.

Such monitoring is accomplished in the illustrated apparatus by employing a pair of dedicated, pressure-sensing ports in the region of the coating enclosure. In the illustrated embodiment, an upper pressure sensing port 70 is provided in the form of an elongated passageway which extends through the upper insert 34, and a lower pressure-sensing port 72 is provided via a long passageway in the lower insert 28. The lower port 72 is preferably located in the lower one-half of the volumetric region of the bed or below the bed, and it is more preferably located in the lower 25% of the volume of the bed. The upper port 70 and the lower port 72 are respectively connected via tubing 74, 76 to a pressure transducer 78 for measuring the pressure at these ports and comparing the two pressures measured to determine the difference between the two measured pressures. If desired, optional, visually-readable gauges can be included. Although a pressure transducer 78 is preferred, other suitable pressure-measuring devices, such as manometers, can alternatively be used. To keep the ports and the tubing clear of dust, carbonaceous material and/or particles, an appropriate slow purge flow of inert gas (not shown) is maintained through both port systems. Purge flows for each of the ports 70, 72 are constant, with purge gas being appropriately injected into the tubings 74, 76. An initial pressure measurement is taken at the beginning of each coating run that takes the respective purge flow into consideration, and it serves as a reference point for that coating run.

A signal from the pressure transducer 78 is sent through a suitable line 84 to a control unit 86. The control unit 86 compares the signal being received with the values programmed into its memory to see if the desired pattern is being maintained, and if deviation is detected, the control unit 86 instigates appropriate adjustments. Adjustments to the surface area of the bed are made by changing the rate at which hydrocarbon is fed to the bed as a part of the fluidized gas flow, or by changing the rate at which particles are supplied to and/or withdrawn from the coater. The amount of hydrocarbon being supplied to the coating zone may be changed within ±10% of its initial value without measurably affecting the pyrocarbon properties; however, such change will have a very significant effect upon the rate of deposition. Therefore, if it is desired to maintain a constant bed surface area by controlling the flow rate of hydrocarbon, the control unit 86 is connected by a suitable line 90 through which a signal, preferably electric, is transmitted to the control valve 48, which determines the rate of flow of hydrocarbon through the inlet conduit 54.

It is generally convenient to set the particle feeder 40 to feed particles of a desired size into the coater 20 at a substantially constant rate, and a control line 88 leading to the feeder 40 is provided for this purpose. Therefore, when it is desired to control the bed surface area by controlling the number of particles in the coating zone, it is preferred to alter the rate of removal of particles from the fluidized bed. Details of such control of the bed surface area are set forth in U.S. Pat. No. 5,284,676 (Feb. 8, 1994), the disclosure of which is incorporated herein by reference. The load cell 65 under the beaker 63 into which the removed particles fall is connected by suitable control line 94 to the control unit 86 and provides a signal which is indicative of the total weight of beaker plus particles. The control unit compares the weight versus time and thereby determines whether the precise amount of particles intended has been removed during each preset interval of time, for example, each 30 or 60 seconds. As a result of this precise reading which is accomplished by using the load cell 65, the control unit 86 will normally cause minor changes to be made (either by varying the rate of flow of nitrogen upward through the particle removal conduit 60 or by varying the off-on intervals if a high gas flow is used to periodically halt particle removal) whenever needed to maintain the desired rate of withdrawal of particles throughout the coating run.

Should a fluidized bed become too small, the actual bed temperature will decrease and the bed may no longer be able to properly levitate the objects being coated, in which case there will be danger that the entire bed will collapse. It has been found that if the surface area of the bed is maintained substantially constant, unalloyed pyrocarbon of certain desired physical properties can be deposited by carrying out pyrolytic deposition under certain parameters. By monitoring the pressure across the bed, it is possible to promptly detect a decrease in the bed surface area as soon as it begins, and the control unit 86 will promptly and automatically effect countermeasures so as to return the surface area of the bed to its desired size, as by slowing the rate of removal of particles from the bed. As a result, the surface area of the bed will promptly gradually increase until the desired size of bed surface area is re-established. On the other hand, if the surface area of the bed were to grow excessively large, the actual bed surface temperature would increase, the characteristics of the pyrocarbon being deposited would also undesirably change, and the rate of deposition of carbon on the heart valve bodies and occluders would slow. Such is also undesirable; accordingly, it is considered important to prevent the bed surface area from growing oversized. Accordingly, when the control unit senses a change in the pressure difference across the bed indicative of an undesirable increase of the surface area above the target size, countermeasures are likewise promptly automatically effected to increase the rate of removal of particles from the bed until the target differential pressure is re-established.

Any suitable electronic controller can be used, such as one commercially available from Inotek/Analog Devices, a UDC 9000 Multi-Pro from Honeywell, or an IBM 386 or 486 computer and Control E.G. software. By monitoring for changes in pressure difference indicative of changes in bed size and immediately effecting compensating changes, as necessary, to return the bed to the target size, the rate of deposition and the properties of unalloyed pyrocarbon being deposited are very carefully controlled throughout an entire run of several hours in length. Coatings of unalloyed pyrocarbon having the desired improved mechanical properties can be uniformly deposited during an individual coating run so as to have a minimum thickness of at least about 0.1 mm of pyrocarbon and preferably at least about 0.2 mm in key regions that will be subjected to wear in heart valves or the like. The thickness of the deposit will be in part dependent upon the overall size of the substrate, and the pyrocarbon may be at least 0.5 millimeter thick and often about 1 mm or more in thickness when larger objects are being coated. It is possible to repeatedly coat objects with unalloyed pyrocarbon coatings having these improved physical properties and having carefully controlled precise thickness to within about 1 mil (0.001 inch). This is particularly valuable when coating parts for prosthetic heart valves wherein precision in achieving uniform physical properties and tolerances is extremely important and thus commercially very valuable.

Although a pressure transducer 78 is the preferred device for monitoring the pressure above the bed and either just below or in a lower region of the bed, other suitable pressure sensing devices can be employed as indicated hereinbefore. It has also been found to be satisfactory to have the pressure transducer 78 simply monitor atmospheric pressure outside the coating apparatus 20, instead of monitoring the pressure just above the particle region of the bed in the enclosure, because under these circumstances the pressure therein is essentially atmospheric. Monitoring atmospheric pressure and comparing it with the pressure in the lower region of the bed monitored via the conduit 72 and feeding a signal representative of the difference between these two values to the control unit 86 provides an adequate alternative way of making measurements to detect changes in the bed size for which immediate compensation is effected in order to precisely obtain the coating characteristics and thicknesses desired in a pyrocarbon deposition run.

Pyrocarbon is, by definition, deposited by the high temperature pyrolysis of a carbon-containing substance; it is thus required that the substrate upon which deposition occurs be stable at the fairly high temperatures to which it will be subjected during pyrolysis. Substrates of commercially available isotropic artificial graphite, such as that sold as AFX-5Q and AFX-5Q-10W by the POCO Graphite Company, of Decatur, Tex., are preferred. However, other artificial graphites having a density between about 1.7 and about 2.1 $g/cm^3$ which are close to perfectly isotropic, e.g. having an isotrophy of about BAF 1.1 or less, can be used.

Hydrocarbons are the preferred carbon-containing substances for pyrolysis, and hydrocarbons having 1 to about 5 carbon atoms, for example propane, propylene, isobutane, pentane, ethane and methane will pyrolyze at temperatures between about 1000° C. and about 1325° C. Particular hydrocarbons that are employed may somewhat vary the characteristics of the pyrocarbon deposited, as can the carbon content of the coating atmosphere. The latter is generally controlled by controlling the concentration of the hydrocarbon gas, usually using a mixture of a hydrocarbon gas, i.e. coating gas, and an inert levitating gas, such as nitrogen, helium or argon or a mixture thereof, although 100% methane may be used. It has been found that the pyrocarbon characteristics desired can be perhaps best obtained by employing a mixture of a hydrocarbon, preferably having a carbon chain length between 2 and 4 carbon atoms, in combination with at least about 40 volume percent of an inert gas and preferably at least about 60%. The preferred hydrocarbon gas which is employed is propane, propylene, isobutane or ethane or a mixture thereof. For example, a mixture of nitrogen and propane containing from about 25% to about 60 volume % of propane may be used.

Whereas previously it had been thought the hardness of pyrocarbon followed the density so that pyrocarbons having sufficiently high hardness to provide the necessary wear resistance for heart valve components and the like would be found only in pyrocarbons having a density of about 2 grams per $cm^3$ or above, it has now been unexpectedly found that there is a region of coating condition parameters where coating of unalloyed pyrocarbon occurs having a density as low as about 1.85 grams per $cm^3$ wherein these carbons exhibit hardness of about 220 DPH or higher, which have properties that are adequate for wear resistance. Even more surprisingly, these carbons have been found to exhibit toughness which is as much as about 50% higher than silicon-alloyed pyrocarbons of comparable hardness and to have flexural strength up to about 20% greater than similar silicon-alloyed pyrocarbons. As a result, these unalloyed pyrocarbons are considered to be more than just the equivalent of silicon-alloyed pyrocarbons containing between about 5 and about 12 weight % silicon, thus making them particularly valuable in this respect for biomedical applications where silicon is undesirable from the standpoint of potential thrombogenicity. Moreover, from a fracture mechanic's point of view, an increase in toughness of 20% would have been a significant advance, and the observed 50% increase is remarkable indeed.

Unalloyed pyrocarbons having these improved physical features, can be deposited in fluidized beds when the sight-port temperature is set at a range between about 1325° and about 1450° C. However, from an overall standpoint the sight-port temperature is preferably maintained between about 1350° and about 1425° C., more preferably at about 1375°–1425° C., and the bed is controlled so the surface temperature is held at a substantially constant value by carefully maintaining a constant bed surface area. By substantially constant is meant that the bed surface temperature does not deviate more than about 25° C. and preferably not more than about 15° C. from the original set point at the beginning of the particular coating step.

It is likewise important that a relatively high surface area to volume ratio be maintained in the coating region so that isotropic pyrocarbon having these desired physical properties will be deposited, and it has been found that the ratio of the bed surface area in square centimeters to the volume of the coating region in cubic centimeters should be between about 10:1 and about 50:1, and preferably between about 20:1 and about 40:1. The bed volume may vary within a coating enclosure of given size with substantial changes in the flow rate of the levitating stream through the bed, because a faster rate of flow will further expand the bed. For example, a 300 gram charge of pyrocarbon coated zirconium oxide particles of the size range indicated above will have a surface area of about 12,060 square centimeters; for such a charge, it may be desirable to employ a flow of the coating-levitating gas of at least about 15 liters per minute up to a flow of about 20–25 L/min in a 3.5 inch I.D. coater. At flow rates between about 15–20 L/min, the bed will occupy a volume of about 475 to 520 cubic centimeters. A charge of about 700 grams of zirconium oxide particles of this type will have a bed surface area of about 28,140 square centimeters, and with a similar flow rate of gas, the bed may occupy a volume of about 680 to about 775 cubic centimeters in a similar coater.

The volume of flow per minute of the mixture of coating gas and fluidizing gas will have an influence upon obtaining the desired ratio of bed surface area to volume in a coater; however, the flow rate is also regulated to supply an approximate amount of carbon to the coating zone per unit time. Generally, for coaters having an interior diameter of up to about 6 inches, it is found to be advantageous to use a flow of between about 0.1 liter and about 0.5 liter, per square centimeter of the cross-sectional area through the cylindrical section of the coating enclosure and preferably between about 0.2 and about 0.4 L/min/cm$^2$. For example, for a coater having a 3.5-inch interior diameter (about 63.6 square centimeters of cross sectional area), it is advantageous to use a flow rate which is between about 15 and about 25 liters per minute of the coating-fluidizing gas mixture, at standard temperature and pressure, taking in consideration the size of the bed. For example, for a bed of about 300 gms of $ZrO_2$ particles as described hereinbefore, a flow rate of the levitating stream of about 15–20 L/min may be preferred. With this flow rate, the volume percentage of coating gas is adjusted to deliver a relatively constant amount of carbon, i.e. the carbon content, to the coating zone per unit time. Therefore, when a particular coating operation runs effectively at 40% propane, a comparable atmosphere composed of about 30% isobutane-70% nitrogen or of about 90–100% methane might be used.

Even within these parameters, it has been found important that the conditions be fairly precisely maintained throughout the coating run so that pyrocarbon having a substantially homogenous crystallite size and isotropy will be deposited. In addition to controlling the bed size for the purpose of maintaining the desired ratios, it is important that the bed size be maintained within strict limits because even small changes in bed size, as indicated hereinbefore, result in distinct changes in the actual temperature at the surface of the substrates where deposition is occurring; such changes in temperature not only affect the rate at which carbon is being deposited but they can affect the physical characteristics of the carbon itself. By precisely controlling these various parameters within the stated limits, it has now been found possible to consistently deposit unalloyed pyrocarbon having outstanding mechanical properties. Young's modulus is usually measured to provide a representative modulus of elasticity for a material such as pyrocarbon, and pyrocarbon having a Young's modulus (which is the ratio of simple tension stress to the resulting strain parallel to the tension, reported in psi×106) between about 3.9 to 4.1 is routinely obtained. The modulus of rupture for bending is the maximum stress per unit area that a specimen can withstand without breaking when it is bent, and it is usually reported in psi×10$^3$ for these materials. This is sometimes referred to as flexural strength, and unalloyed pyrocarbons made under these parameters can have a modulus of rupture of about 58 to 64 or higher. Hardness was earlier discussed, a pyrocarbon should have a DPH of at least about 200 in order to be considered to be adequate to provide the desired wear resistance over the life of a heart valve component. These pyrocarbons are preferably deposited so as to have a hardness of at least about 220 DPH and more preferably a DPH of about 230 or higher, e.g. up to about 250. They should also be isotropic, having a BAF of not greater than about 1.1 and preferably between 1.0 and about 1.075. Another important physical property for pyrocarbon is the measurement of strain to failure; whereas silicon-alloyed pyrocarbon generally had a strain-to-failure of about 1.2%, these unalloyed pyrocarbons have a strain-to-failure of about 1.3 to 1.4%, which is a significant increase for this property. $K_{IC}$ is a value which is sometimes referred to as fracture toughness; it is a measure of the force required to propagate an existing small crack in pyrocarbon and is usually reported in units of Ksi (1000 psi)×$\sqrt{in}$, or alternatively as MPa($\sqrt{m}$). It has been found that unalloyed pyrocarbons are produced using the aforementioned temperature range and conditions that have a fracture toughness as much as about 50% higher than present commercial isotropic pyrolytic carbon coatings; these commercial coatings that contain an alloying amount of about 7 weight % of silicon have a $K_{IC}$ of about 1.05. Thus, not only is the need for silicon-alloying in pyrocarbons to be used for biomedical purposes eliminated but at the same time, a 50% improvement in toughness is achieved—a truly surprising and totally unexpected result.

The following are examples of the operation of a fluidized bed coating apparatus in a manner so as to carry out processes for depositing pyrocarbon embodying various features of the present invention.

EXAMPLE 1

When a coating run is ready to begin, a predetermined bed size is established by loading a precise amount of pyrocarbon-coated $ZrO_2$ particles to provide the desired amount of surface area and setting the temperature and the flow rates of inert gas (nitrogen) and hydrocarbon (propane), as well as setting a constant rate of feeding particles and a nominal rate of withdrawal of particles. This is all conveniently done through the control unit via control lines 91 and 93, which respectively lead to the adjustable valves 52 and 68. A fluidizing flow of an inert gas, such as nitrogen, is established upward through the coater 20 by setting the valve 52 via the control line 91 to supply nitrogen at a desired rate of flow from the source 50, which may be a pressurized tank or the like. A suitable charge of particles is then added to the coater, through the upper end, to create a fluidized bed having the desired amount of surface area. For example, in a coater having an internal coating enclosure diameter of about 3½ inches, one may begin with a charge of about 250 to about 700 grams of pyrocarbon-coated zirconium dioxide particles having sizes greater than about 325 microns but less than about 850 microns. The particles of this initial bed are preferably pyrocarbon-coated versions of the uncoated zirconia particles that will subsequently be fed into the bed during coating. Uncoated particles which have a density of about 5.37 grams per cm$^3$ and a preferred size ranging from about 300 microns to about 425 microns (with an average size of about 360 microns) are loaded into the particle feeder 40. For a typical coating operation in a coater of about this size, about 20 to 40 heart valve orifice rings are added to the bed; such rings, when coated, will serve as valve bodies for prosthetic heart valves. Exemplary orifice rings generally have the form of short tubes, having a height of about 0.7 cm., an I.D. of about 1.5 to 2.5 cm., and an O.D. of about 1.6 to 2.6 cm. U.S. Pat. Nos. 5,152,785 and 5,192,309 show generally representative heart valves having valve bodies of this general type. The substrates to be coated are added after the particle bed has been brought up to its operating temperature of about 1400° C. using the induction heating apparatus 44.

The coating apparatus is then operated until both the particles and the objects reach the desired temperature. During this warmup period, the control unit via the control line 93 causes a sufficient flow of nitrogen to be maintained upward through the conduit 56, which has an entrance aperture in the form of about a 3/16 inch inner diameter open upper end, to prevent particle withdrawal. A purge flow rate, as high as about 4 liters per minute, of nitrogen is maintained through the lower pressure port 72 so as to prevent particles from entering this port. The exit conduit 56 is located so that its open upper end is located about 0.4 inch below the top edge of the conical surface 30 of the lower insert 28, wherein it is in about the middle of the bed. For a levitating gas flow of about 25 liters per minute through this coating enclosure wherein the conical surface of the lower insert has a vertical height of about 5 inches, when a 700 gram charge of coated $ZrO_2$ particles is used along with 40 orifice rings, the bed may occupy a volume of about 700–800 cubic centimeters.

When a coating run is ready to begin, the control unit 86 causes the valve 48 to be opened to its predetermined set point, as desired for this particular run, and flow of a preferred coating gas, i.e. propane, is begun so that a mixture of it and the fluidizing gas that is already flowing through the line 54 into the central passageway 32 is being supplied at the desired rates of flow. The flow rates of the inert gas and propane are set so that the flow of the fluidizing-coating gas mixture upward through the coating enclosure, measured at standard temperature and pressure, is about 14 liters/minute of nitrogen and about 7 liters/minute of propane, for a total flow of about 21 liters/min. As soon as the coating run begins, the feeder 40 is caused to feed uncoated zirconia particles into the apparatus at a constant rate of about 2.0 grams per minute via the entrance passageway 42 through which they fall to become a part of the fluidized bed. Because of their greater density, the small uncoated particles 41 quickly gravitate to a lower level in the bed. The control unit 86, via the valve 68 and the control line 93, controls the amount of nitrogen which flows upward through the particle discharge passageway 60 so that particles are withdrawn at an initial rate of about 7 grams per minute, which rate is maintained until the control unit detects changes are occurring in the bed surface area. A purge flow of about 4 liters of nitrogen per minute is maintained through the entrance passageway 42, flowing along with the falling zirconia particles, and a purge flow of about 1 liter of nitrogen per minute is maintained through the tubing 74 leading to the upper pressure sensing port 70.

The pressure difference between the lower port 72 and the upper port 70 is monitored throughout the coating run by a pressure transducer 78 (e.g. a commercially available Sensotec Model Z or a SETRA Model C239). An output signal from the transducer which is representative of the difference in measured pressures is transmitted to the electronic controller 86, and it is compared, for example, each 15 seconds, with a program that is representative of the desired bed size. The control unit 86 thus monitors the pressure differential, and, as soon as changes are detected, it causes appropriate adjustments to be made in the rate of withdrawal of particles from the coating enclosure. This monitoring and the instigation of countermeasures to changes in bed surface area continues throughout the entire coating run, which may typically take between about two and about four hours. For example, when an increase in pressure differential is detected above the target value which is indicative that growth in the bed surface area has occurred, the control unit 86 acts to compensate for this growth by removing particles at a slightly faster rate.

The exemplary coating operation is carried out for about 180 minutes under conditions so as to initially maintain desired bed surface area throughout the entire coating run. At the conclusion of the coating run and cool-down, the coated articles are examined and the pyrocarbon is found to be of high quality and to have a precise uniform thickness of substantially 0.010 inch, having a tolerance within about 0.001 inch of the desired value.

The pyrocarbon deposited has a hardness of about 235 DPH, and it is considered to be satisfactory from a standpoint of providing adequate wear resistance for heart valve components. The flexural strength is about $64 \times 10^3$ psi, and the modulus of elasticity is about $3.9 \times 10^6$ psi. The toughness is excellent, showing a $K_{IC}$ of about 1.58. The strain-to-failure is about 1.4%. These unalloyed pyrocarbon-coated components are considered to be well suited for use as valve bodies in mechanical heart valves.

EXAMPLE 2

The pyrocarbon deposition process set forth in Example 1 is repeated using a temperature of about 1400° C. and a mixture of about 40 volume % propane and about 60 volume % nitrogen at a flow rate of about 20 liters per minute. A charge of pyrocarbon-coated zirconium oxide particles of about 500 grams is employed along with about 10 flat graphite rectangular slabs which are provided as the substrates for coating to allow precise measurement of carbon properties. Coating is carried out for a sufficient time to deposit a pyrocarbon coating having a thickness of about 0.01 inch; the coatings are uniform and have a tolerance within about 0.001 inch. The pyrocarbon deposited has a hardness of about 235 DPH and a density of about 1.89 gm/cm$^3$ and it is considered to be satisfactory from a standpoint of providing adequate wear resistance for heart valve components. The flexural strength is about $63.2 \times 10^3$ psi, and the modulus of elasticity is about $3.9 \times 10^6$ psi. The toughness is excellent, showing $K_{IC}$ of about 1.6. The strain-to-failure is about 1.38%. The properties of these unalloyed pyrocarbon-coated substrates are such that components, such as valve bodies and occluders, made under these conditions are considered to be well suited for use as valve bodies in mechanical heart valves.

EXAMPLE 3

The pyrocarbon deposition process set forth in Example 1 is repeated using a temperature of about 1400° C. and a mixture of about 40.5 volume % ethane and about 59.5 volume % nitrogen at a flow rate of about 20 liters per minute. A charge of pyrocarbon-coated zirconium oxide particles of about 500 grams is employed along with about 10 flat graphite rectangular slabs which are provided as the substrates for coating to allow precise measurement of carbon properties. Coating is carried out for a sufficient time to deposit a pyrocarbon coating having a thickness of about 0.01 inch; the coatings are uniform and have a tolerance within about 0.001 inch. The pyrocarbon deposited has a hardness of about 235 DPH and a density of about 1.91 gm/cm$^3$, and it is considered to be satisfactory from a standpoint of providing adequate wear resistance for heart valve components. The flexural strength is about $62.6 \times 10^3$ psi, and the modulus of elasticity is about $3.9 \times 10^6$ psi. The toughness is excellent, showing $K_{IC}$ of about 1.59. The strain-to-failure is about 1.38%. The properties of these unalloyed pyrocarbon-coated substrates are such that components, such as valve bodies and occluders, made under these conditions are considered to be well suited for use as valve bodies in mechanical heart valves.

EXAMPLE 4

The pyrocarbon deposition process set forth in Example 1 is repeated using a temperature of about 1400° C. and a mixture of about 30 volume % isobutane and about 70 volume % nitrogen at a flow rate of about 20 liters per minute. A charge of pyrocarbon-coated zirconium oxide particles of about 500 grams is employed along with about 10 flat graphite rectangular slabs which are provided as the substrates for coating to allow precise measurement of carbon properties. Coating is carried out for a sufficient time to deposit a pyrocarbon coating having a thickness of about 0.01 inch; the coatings are uniform and have a tolerance within about 0.001 inch. The pyrocarbon deposited has a hardness of about 235 DPH and a density of about 1.95 gm/cm$^3$, and it is considered to be satisfactory from a standpoint of providing adequate wear resistance for heart valve components. The flexural strength is about $62.3 \times 10^3$ psi, and the modulus of elasticity is about $3.9 \times 10^6$ psi. The toughness is excellent, showing $K_{IC}$ of about 1.58. The strain-to-failure is about 1.37%. The properties of these unalloyed pyrocarbon-coated substrates are such that components, such as valve bodies and occluders, made under these conditions are considered to be well suited for use as valve bodies in mechanical heart valves.

EXAMPLE 5

The pyrocarbon deposition process set forth in Example 1 is repeated using a temperature of about 1400° C. and of about 100 volume % methane at a flow rate of about 20 liters per minute. A charge of pyrocarbon-coated zirconium oxide particles of about 500 grams is employed along with about 10 flat graphite rectangular slabs which are provided as the substrates for coating to allow precise measurement of carbon properties. Coating is carried out for a sufficient time to deposit a pyrocarbon coating having a thickness of about 0.01 inch; the coatings are uniform and have a tolerance within about 0.001 inch. The pyrocarbon deposited has a hardness of about 222 DPH and a density of about 2.07 gm/cm$^3$, and it is considered to be satisfactory from a standpoint of providing adequate wear resistance for heart valve components. The flexural strength is about $57.5 \times 10^3$ psi, and the modulus of elasticity is about $4.0 \times 10^6$ psi. The toughness is excellent, showing $K_{IC}$ of about 1.58. The strain-to-failure is about 1.29%. The properties of these unalloyed pyrocarbon-coated substrates are such that components, such as valve bodies and occluders, made under these conditions are considered to be well suited for use as valve bodies in mechanical heart valves.

EXAMPLE 6

The pyrocarbon deposition process set forth in Example 1 is repeated using a temperature of about 1425° C. and a mixture of about 40 volume % propane and about 60 volume % nitrogen at a flow rate of about 20 liters per minute. A charge of pyrocarbon-coated zirconium oxide particles of about 500 grams is employed along with about 10 flat graphite rectangular slabs which are provided as the substrates for coating to allow precise measurement of carbon properties. Coating is carried out for a sufficient time to deposit a pyrocarbon coating having a thickness of about 0.01 inch; the coatings are uniform and have a tolerance within about 0.001 inch. The pyrocarbon deposited has a hardness of about 226 DPH and a density of about 1.81 gm/cm$^3$, and it is considered to be satisfactory from a standpoint of providing adequate wear resistance for heart valve components. The flexural strength is about $61.8 \times 10^3$ psi, and the modulus of elasticity is about $3.7 \times 10^6$ psi. The toughness is excellent, showing $K_{IC}$ of about 1.58. The strain-to-failure is about 1.38%. The properties of these unalloyed pyrocarbon-coated substrates are such that components, such as valve bodies and occluders, made under these conditions are considered to be well suited for use as valve bodies in mechanical heart valves.

EXAMPLE 7

The pyrocarbon deposition process set forth in Example 1 is repeated using a temperature of about 1450° C. and a mixture of about 40 volume % propane and about 60 volume % nitrogen at a flow rate of about 20 liters per minute. A charge of pyrocarbon-coated zirconium oxide particles of about 500 grams is employed along with about 10 flat graphite rectangular slabs which are provided as the substrates for coating to allow precise measurement of carbon properties. Coating is carried out for a sufficient time to deposit a pyrocarbon coating having a thickness of about 0.01 inch; the coatings are uniform and have a tolerance within about 0.001 inch. The pyrocarbon deposited has a hardness of about 208 DPH and a density of about 1.83 gm/cm$^3$, and it is considered to be satisfactory from a standpoint of providing adequate wear resistance for heart valve components. The flexural strength is about $54 \times 10^3$ psi, and the modulus of elasticity is about $3.5 \times 10^6$ psi. The toughness is excellent, showing $K_{IC}$ of about 1.54. The strain-to-failure is about 1.33%. The properties of these unalloyed pyrocarbon-coated substrates are such that components, such as valve bodies and occluders, made under these conditions are considered to be well suited for use as valve bodies in mechanical heart valves.

EXAMPLE 8

The pyrocarbon deposition process set forth in Example 1 is repeated using a temperature of about 1375° C. and a mixture of about 40 volume % propane and about 60 volume % nitrogen at a flow rate of about 20 liters per minute. A charge of pyrocarbon-coated zirconium oxide particles of about 500 grams is employed along with about 10 flat graphite rectangular slabs which are provided as the substrates for coating to allow precise measurement of carbon properties. Coating is carried out for a sufficient time to deposit a pyrocarbon coating having a thickness of about 0.01 inch; the coatings are uniform and have a tolerance within about 0.001 inch. The pyrocarbon deposited has a hardness of about 231 DPH and a density of about 1.96 gm/cm$^3$ and it is considered to be satisfactory from a standpoint of providing adequate wear resistance for heart valve components. The flexural strength is about 63×10$^3$ psi, and the modulus of elasticity is about 3.9×10$^6$ psi. The toughness is good, showing a $K_{IC}$ of about 1.18. The strain-to-failure is about 1.41%. The properties of these unalloyed pyrocarbon-coated substrates are such that components, such as valve bodies and occluders, made under these conditions are considered to be well suited for use as valve bodies in mechanical heart valves.

EXAMPLE 9

The pyrocarbon deposition process set forth in Example 1 is repeated using a temperature of about 1350° C. and a mixture of about 40 volume % propane and about 60 volume % nitrogen at a flow rate of about 20 liters per minute. A charge of pyrocarbon-coated zirconium oxide particles of about 500 grams is employed along with about 10 flat graphite rectangular slabs which are provided as the substrates for coating to allow precise measurement of carbon properties. Coating is carried out for a sufficient time to deposit a pyrocarbon coating having a thickness of about 0.01 inch; the coatings are uniform and have a tolerance within about 0.001 inch. The pyrocarbon deposited has a hardness of about 226 DPH and a density of about 2 gm/cm$^3$, and it is considered to be satisfactory from a standpoint of providing adequate wear resistance for heart valve components. The flexural strength is about 57×10$^3$ psi, and the modulus of elasticity is about 3.9×10$^6$ psi. The toughness is acceptable, showing a $K_{IC}$ of about 0.96. The strain-to-failure is about 1.33%. The properties of these unalloyed pyrocarbon-coated substrates are such that components, such as valve bodies and occluders, made under these conditions are considered to be adequate for use as valve bodies in mechanical heart valves.

EXAMPLE 10

The pyrocarbon deposition process set forth in Example 1 is repeated using a temperature of about 1400° C. and a mixture of about 25 volume % propane and about 75 volume % nitrogen at a flow rate of about 15 liters per minute. A charge of pyrocarbon-coated zirconium oxide particles of about 700 grams is employed along with about 8 flat graphite rectangular slabs which are provided as the substrates for coating to allow precise measurement of carbon properties. Coating is carried out for a sufficient time to deposit a pyrocarbon coating having a thickness of about 0.01 inch; the coatings are uniform and have a tolerance within about 0.001 inch. The pyrocarbon deposited has a hardness of about 240 DPH and a density of about 1.85 gm/cm$^3$ and it is considered to be satisfactory from a standpoint of providing adequate wear resistance for heart valve components. The flexural strength is about 69×10$^3$ psi, and the modulus of elasticity is about 3.9×10$^6$ psi. The toughness is excellent, showing a $K_{IC}$ of about 1.69. The strain-to-failure is about 1.5%. The properties of these unalloyed pyrocarbon-coated substrates are such that components, such as valve bodies and occluders, made under these conditions are considered to be well suited for use as valve bodies in mechanical heart valves.

Although the invention has been described with regard to a number of preferred embodiments, it should be understood that various changes as would be obvious to one having the ordinary skill in this art may be made without departing from the invention which is defined by the claims appended hereto. Although heart valve components have been the subject of many of the illustrations, it should be understood that pyrocarbon having these excellent mechanical properties can be used for many other biomedical applications as well as other applications where the inclusion of an alloying agent, i.e. a metal or metalloid, such as silicon, that forms a carbide, would be considered undesirable. Furthermore, although one significant advantage of the invention is the provision of pyrocarbon having these outstanding mechanical properties and excellent wear resistance without the necessary inclusion of silicon or some other alloying agent to increase hardness, it should be understood that up to about 3 weight % of silicon might be included in these pyrocarbons without adversely affecting the outstanding fracture toughness which they exhibit; accordingly, such carbons would be considered to be equivalents of these pure unalloyed pyrocarbons. Likewise, although the discussion is centered upon the employment of a single hydrocarbon for the coating gas, it should be understood that a mixture of two or more hydrocarbons could be used if desired, and similarly a mixture of two or more inert gases could likewise be employed.

Particular features of the invention are emphasized in the claims that follow.

What is claimed is:

1. A process for coating prosthetic heart valve components with pyrocarbon having high fracture toughness, high flexural strength and high strain-to-failure without including 5 or more weight percent of silicon in such pyrocarbon, which process comprises, establishing a bed of particles in a coating enclosure by levitating said particles so as to create a region within said enclosure wherein coating with pyrocarbon will occur and levitating a plurality of substrates for heart valve bodies or occluders along with said particles in said coating region, said particles providing sufficient surface area that the ratio of surface area of said bed of particles measured in square centimeters to the volume of the coating region measured in cubic centimeters is at least 10 to 1, maintaining said particles and said substrates at a temperature between about 1350° C. and about 1425° C., employing a levitating gas stream which includes a hydrocarbon that will pyrolytically decompose at said temperature and may also include an inert gas but which is substantially devoid of any alloying agent and maintaining a continuous upward flow of said gas stream through said coating region at a rate of between about 0.1 and about 0.5 liter per minute per sq. cm. of cross section of said coating region, said hydrocarbon having a carbon chain length not greater than about 5 carbon atoms, continuing said continuous upward flow of said gas stream through said coating region for a length of time sufficient to deposit a uniform coating having a thickness of at least about 0.2 mm of substantially unalloyed pyrocarbon upon each of said substrates, and maintaining a substantially constant bed surface area within said coating region by adding additional particles thereto while removing therefrom pyrocarbon-coated particles which have grown in particle size as a result of deposition of pyrocarbon so that the actual bed temperature at surfaces where deposition is occurring remains within a temperature range of about 50° C., whereby said substrates remain in said enclosure and are coated with unalloyed pyrocarbon having a density of about 1.8 to about 2.0 g/cm$^3$, a $K_{IC}$ of at least about 1.2, a modulus of rupture for bending of at least about 58, a strain-to-failure of at least about 1.3%, and a Young's modulus of about 4.0× 10$^6$ psi or below.

2. A process according to claim 1 wherein said pyrocarbon has a $K_{IC}$ of at least about 1.54.

3. A process according to claim 1 wherein said substrates are made of isotropic artificial graphite.

4. A process according to claim 1 wherein an inert gas is present and constitutes at least about 40 volume percent of said stream.

5. A process for making unalloyed isotropic pyrocarbon having high fracture toughness, high flexural strength and high strain-to-failure, which process comprises, establishing a bed of particles in a coating enclosure by levitating said particles so as to create a region within said enclosure wherein coating with pyrocarbon will occur and levitating a plurality of substrates to be coated along with said particles in said coating region, said particles providing sufficient surface area that the ratio of surface area of said bed of particles measured in square centimeters to the volume of the coating region measured in cubic centimeters is at least 10 to 1, maintaining said coating region at a set temperature above about 1325° C. and at or below about 1450° C., employing a levitating gas stream which includes a hydrocarbon that will pyrolytically decompose at said temperature and maintaining a continuous upward flow of said gas stream through said coating region at a rate of between about 0.1 and about 0.5 liter per minute per sq. cm. of cross section of said coating region, said hydrocarbon having a carbon chain length not greater than about 5 carbon atoms, continuing said continuous upward flow of said gas stream through said coating region for a length of time sufficient to deposit a uniform coating of a desired thickness of at least about 0.1 mm of pure unalloyed pyrocarbon upon each of said substrates, and maintaining a substantially constant bed surface area within said coating region by adding additional particles thereto while removing therefrom pyrocarbon-coated particles which have grown in particle size as a result of deposition of pyrocarbon, so that the surface temperature of said particles and said substrates remains substantially constant during said length of time, whereby said substrates remain in said enclosure and are coated with unalloyed pyrocarbon having such properties with a density of between about 1.7 and about 2.1 g/cm$^3$, a $K_{IC}$ of at least about 1.2, a modulus of rupture for bending of at least about 58, a strain-to-failure of at least about 1.3%, and a Diamond Pyramid Hardness (DPH) of between about 200 and 250.

6. A process according to claim 5 wherein the amount of said particles is selected so that the ratio of the surface area of said bed of particles measured in square centimeters to the volume of said coating region measured in cubic centimeters is at least about 20 to 1.

7. A process according to claim 6 wherein said ratio is between about 20 to 1 and about 40 to 1.

8. A process according to claim 5 wherein said hydrocarbon is selected from the group consisting of propane, propylene, ethane, methane, butane and mixtures thereof.

9. A process according to claim 5 wherein said gas stream is a mixture of said hydrocarbon and an inert gas devoid of any alloying agent, which inert gas constitutes at least about 40 volume percent of said mixture, and said flow rate is between about 0.2 and about 0.4 L/min/sq.cm.

10. A process according to claim 9 wherein said hydrocarbon and the volume percent of said hydrocarbon are selected so that said pyrocarbon deposited is isotropic and has a hardness of at least about 220 (DPH), and an apparent crystalline size of at least about 30 Å.

11. A process according to claim 10 wherein said isotropic pyrocarbon which is deposited has a Bacon Aniosotropy Factor (BAF) between 1.0 and about 1.1.

12. A process according to claim 11 wherein said deposited pyrocarbon has a density of between about 1.8 and about 1.95 gm/cm$^3$.

13. A process according to claim 5 wherein said temperature is maintained between about 1350° C. and about 1425° C.

14. A process for making substantially unalloyed pyrocarbon having high fracture toughness, high flexural strength and high strain-to-failure, which process comprises, establishing a bed of particles in a coating enclosure by levitating said particles so as to create a region within said enclosure wherein coating with pyrocarbon will occur and levitating a plurality of substrates to be coated along with said particles in said coating region, said particles providing sufficient surface area that the ratio of surface area of said bed of particles measured in square centimeters to the volume of the coating region measured in cubic centimeters is at least 10 to 1, maintaining said particles and said substrates at a temperature between about 1325° C. and about 1425° C., employing a levitating gas stream which is a mixture of a hydrocarbon that will pyrolytically decompose at said temperature and an inert gas and is substantially devoid of any alloying agent, which inert gas constitutes at least about 40 volume percent of said mixture, and maintaining a continuous upward flow of said gas stream through said coating region at a rate of between about 0.1 and about 0.5 liter per minute per sq. cm. of cross section of said coating region, said hydrocarbon having a carbon chain length not greater than about 5 carbon atoms, continuing said continuous upward flow of said gas stream through said coating region for a length of time sufficient to deposit a uniform coating having a thickness of at least about 0.1 mm of substantially unalloyed pyrocarbon upon each of said substrates maintaining a substantially constant bed surface area within said coating region by adding additional particles thereto while removing therefrom pyrocarbon-coated particles which have grown in particle size as a result of deposition of pyrocarbon so that the actual bed temperature at surfaces where deposition is occurring remains within a temperature range of about 50° C., and whereby said substrates remain in said enclosure and are coated with unalloyed pyrocarbon having a density of about 1.8 to about 2.0 g/cm$^3$, a $K_{IC}$ of at least about 1.2, a modulus of rupture for bending of at least about 58, a strain-to-failure of at least about 1.3%, and a Young's modulus of about $4.0 \times 10^6$ psi or below.

15. A process according to claim 14 wherein said pyrocarbon has a $K_{IC}$ of at least about 1.54.

16. A process according to claim 14 wherein said temperature is maintained at between about 1375° C. and about 1425° C.

17. A process according to claim 14 wherein the amount of said particles is selected so that the ratio of the surface area of said bed of particles measured in square centimeters to the volume of said coating region measured in cubic centimeters is at least about 20 to 1.

18. A process according to claim 17 wherein said hydrocarbon is propane, said levitating gas stream upward flow rate is between about 0.2 and about 0.4 liters per sq.cm. per minute, and said coating is continued to deposit a uniform coating of a thickness of at least about 0.2 mm on said substrates.

19. A process according to claim 14 wherein highly isotropic pyrocarbon is deposited having a BAF not greater than 1.075 and a hardness of at least about 230 (DPH).

* * * * *